United States Patent [19]

Williams

[11] Plant 4,581

[45] Jul. 29, 1980

[54] MINIATURE ROSE PLANT

[76] Inventor: Ernest D. Williams, 1510 Lebanon Ave., Dallas, Tex. 75208

[21] Appl. No.: 33,845

[22] Filed: Apr. 27, 1979

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized by the bright orange color of buds and flowers and bi-color effect of the upper and lower petal surface.

1 Drawing Figure

1

The present invention relates to a new and distinct variety of hardy, dwarf, bush type rose plant of the miniature class; the variety being primarily characterized — as to novelty — by light to medium orange color buds and flowers with lighter (creamy) reverse which in general color effect are similar to Gloriglo, miniature (U.S. Plant Pat. No. 4,305).

The variety is further characterized by:

An abundance of bloom, with flowers borne singly (occasionally several) to the stem.

Light to moderate fragrance.

A plant which is vigorous, of rounded somewhat spreading shape with semi-glossy (to matt) small foliage with pointed leaflets; the buds and flowers being similar in form and size to Gloriglo (miniature — U.S. Plant Pat. No. 4,305).

The plant, which has a normal height of 12–14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a cross between an un-named seedling as the seed parent and Over The Rainbow - miniature (U.S. Plant Pat. No. 3,472), as the pollen parent.

Subsequent to origination of the variety I successfully asexually reproduced it at my nursery, located as aforesaid, by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety name.*—Cupid's Beauty.

Flowers borne: singly (occasionally several) on slender, wirey stems.

2

Quantity of bloom: Abundant both outside and in greenhouse.

Bud:

*Peduncle.*—Medium to long; slender but sturdy; erect; medium to light green; hairs — few or none.

*Before calyx breaks.*—Size — small. Form long: pointed with several foliaceous apendages on surface of bud; with foliaceous parts extending beyond the tip of the bud equal to one-half or less of its length. Color — medium green.

*As calyx breaks.*—Color — creamy, blending into orange at tip. Opening: opens well in all weather.

Bloom:

*Size when fully open.*—Small, averaging about 1 1/16".

*Petalage.*—Averaging about 40–45 petals, arranged regularly plus sometimes occasional petaloids.

*Form.*—High centered with petals rolled loosely outward, and later at maturity full and somewhat rounded. Open flowers may show stamens.

Petals: Fairly thick; satiny on inside and on outside surface.

*Shape.*—Outside petals, broad lanceolate (nearly round) with acute tip; intermediate — broad lanceolate with short acute tip; inside — lanceolate with acute or rounded tip.

Color: Newly opened flower from a plant grown outdoors;

*Outside petal.*—Outside surface — creamy white, tinted with pink and orange on outer (away from base) ½ or more of petal — this coloring caused by bleeding of deeper color from upper surface, becoming slightly greenish toward base. Inside surface — similar to Mars Orange 013 blended or shaded with a red shade similar to Vermillion 18/1, and often tinted or blended with darker near plum shades near petal edges, but usually (on the live flower) more "alive" and a bit more red — blending into cream and soft greenish yellow on basal ⅓ of petal.

*Intermediate petal.*—Outside surface — similar to outside petal. Inside surface — similar to but tending to be lighter shade than outside petal.

*Inner petal.*—Outside surface — same as intermediate petal; inside surface — same as intermediate petal. Note: There is no exact color on chart used to match the changing color or blend of colors of this variety. General color effect; newly opened flowers — color orange to orange red. Three days open — color similar to newly opened flowers but deeper color (outdoors). Behavior — opens well in all weather. Spent petals drop off. Flower longevity (May 1978) — plant in pot 6–8 days. Cut flowers at living room temperature 4–6 days.

Reproductive organs:

*Stamens.*—Few, arranged regularly about pistils.

*Filaments.*—Varying length, medium to long, yellow.

*Anthers.*—Few or none.

*Pollen.*—Little or none.

*Pistils.*—Average number.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes seven) leaflets — small; leathery; semi-glossy to matt.

*Leaflets.*—Shape: broad lanceolate; nearly oval; apex acute; base rounded or rounded acute. Margin serrate. Color: deep green; new growth — reddish to bronze. Rachis: medium strength; upper side may have a few tiny short hairs or prickles. Stipules: medium long; narrow to medium width; short length narrow points which turn out usually at more than 45 degrees.

Growth:

*Habit.*—Dwarf; bushy; rounded; much branched.

*Growth.*—Free; vigorous; internodes short.

*Canes.*—Medium; slender; sturdy.

*Main stems.*—Color: medium green.

*Thorns.*—Few; small; slender. Prickles — few or none; hairs — none.

*Branches.*—Color: light to medium green. Thorns: few; small; slender. Medium to short oval base. Prickles: none. Hairs: usually none.

*Young shoots.*—Color: bronze or reddish. Thorns: few or none.

The miniature rose plant and its flower as herein described may vary in slight detail due to climatic, soil and cultural conditions under which the variety may be grown; the present description being of the variety as grown at Dallas, Tex., and at Visalia, Calif.

The following is claimed:

1. A new and distinct variety of miniature rose plant of hardy, dwarf, bushy, rounded, much branched habit, substantially as illustrated and described, characterized by buds and flowers which are of an orange or orange blend coloring, the buds and flowers resembling Gloriglo (Miniature — U.S. Plant Pat. No. 4,305) in size and color, the present variety having more petals, and a more compact plant habit, the mature flowers often aging quite red in cooler weather; and further characterized by a plant which is easy to propagate from soft wood cuttings, with an abundance of flowers usually borne singly on slender wirey stems.

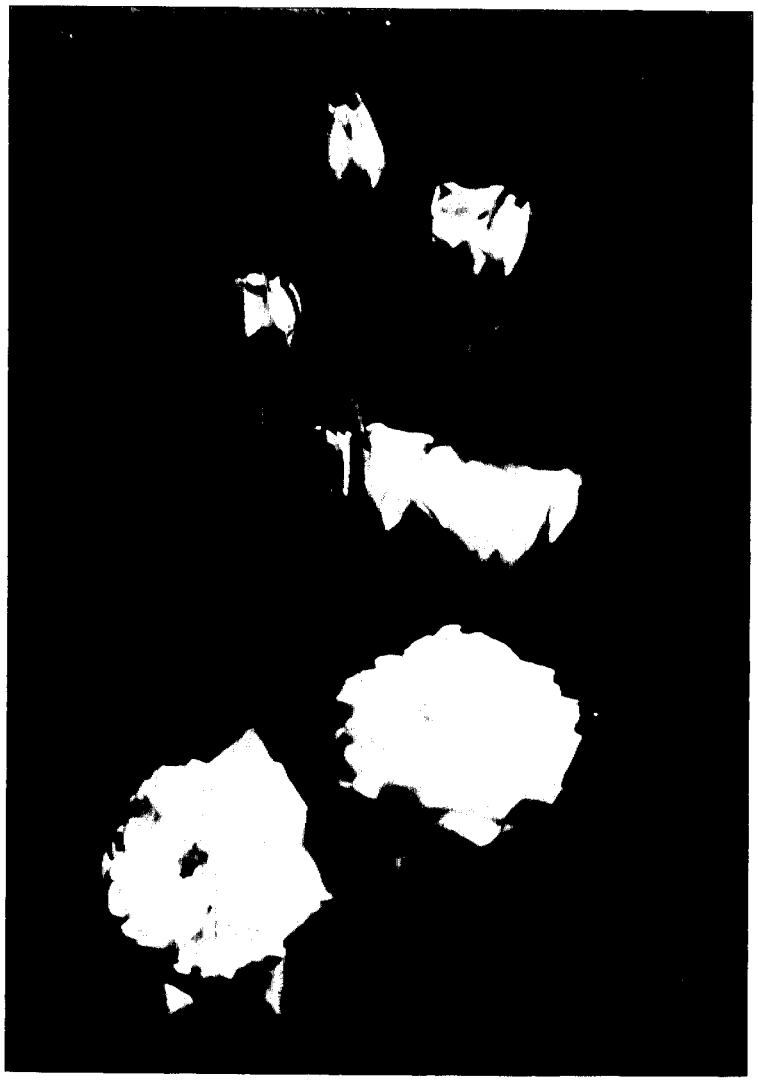

* * * * *